United States Patent [19]
Vilardi et al.

[11] Patent Number: 5,211,808
[45] Date of Patent: May 18, 1993

[54] MICROWAVE HEATING IN A VACUUM CENTRIFUGAL CONCENTRATOR

[75] Inventors: Frank Vilardi, Holbrook; James Boncore, Sayville; Silvio Bellotti, New Hyde Park; Yury Zlobinsky, Massapequa, all of N.Y.

[73] Assignee: Savant Instruments, Farmingdale, N.Y.

[21] Appl. No.: 614,074

[22] Filed: Nov. 13, 1990

[51] Int. Cl.⁵ .............................................. B01D 1/00
[52] U.S. Cl. .................... 159/6.1; 159/16.1; 159/DIG. 16; 159/DIG. 26; 159/DIG. 42; 219/10.55 A; 219/10.55 F; 219/10.55 R; 202/205; 333/230; 494/26; 494/61; 494/84
[58] Field of Search ............... 159/6.1, 16.1, DIG. 16, 159/DIG. 26, DIG. 42; 202/205, 269, 267.1; 494/26, 38, 61, 84, 16; 219/10.55 A, 10.55 F, 10.55 R; 34/92; 203/86, 91, 100; 333/230

[56] References Cited

U.S. PATENT DOCUMENTS

| | | | |
|---|---|---|---|
| 2,566,274 | 8/1951 | White et al. | 159/DIG. 26 |
| 2,953,457 | 9/1960 | Sanna | 159/DIG. 26 |
| 3,204,687 | 9/1965 | Sargeant | 159/DIG. 26 |
| 3,607,667 | 9/1971 | Knapp et al. | 159/DIG. 26 |
| 4,184,060 | 1/1980 | Lembens | 34/1 |
| 4,226,669 | 10/1980 | Vilardi | 159/6.1 |
| 4,294,624 | 10/1981 | Veltman | 159/DIG. 26 |
| 4,347,670 | 9/1982 | Wear et al. | 34/1 |
| 4,488,935 | 12/1984 | Ruhe | 202/205 |
| 4,549,053 | 10/1985 | Haugh | 159/DIG. 26 |
| 4,710,266 | 12/1987 | Hayashi et al. | 159/DIG. 12 |
| 4,967,486 | 11/1990 | Doelling | 34/1 |
| 5,137,604 | 8/1992 | Meeks et al. | 159/6.1 |

FOREIGN PATENT DOCUMENTS 1074116  6/1967  United Kingdom ....... 159/DIG. 26

Primary Examiner—Virginia Manoharan
Attorney, Agent, or Firm—Morrison Law Firm

[57] ABSTRACT

A vacuum concentrator uses microwave heating to enhance the rapid drying of a liquid specimen. Microwave heating without excessive arcing is made possible in a vacuum chamber by controlling the power of a microwave generator, by modifying antenna-like objects, and by interposing air in a direct path between opposing edges of microwave injection slots, while maintaining the vacuum condition in the vacuum chamber. This can be accomplished by using air filled plastic bosses passing through, and substantially filling the microwave injection slots. An alternate to the air filled bosses can be a non-metallic closure plate that excludes the microwave injection slots from the vacuum chamber, while allowing energy to be injected freely into the chamber. The microwave heating energy is absorbed by a vacuum chamber cover and dissipated to the atmosphere as heat.

17 Claims, 7 Drawing Sheets

MICROWAVE HEATING IN A VACUUM CENTRIFUGAL CONCENTRATOR

BACKGROUND OF THE INVENTION

The present invention relates to an apparatus for removal of water or other liquids and concentration of a substance, and more particularly to a vacuum centrifugal concentrator, and still more particularly to a vacuum centrifugal concentrator that heats the substance being processed to enhance the concentration procedure.

The use of vacuum centrifugal concentrators for removing moisture from a liquid substance to provide a dry specimen for analysis is well known. Such a device is fully disclosed in U.S. Pat. No. 4,226,669, the disclosure of which is herein incorporated by reference for background material. However, the effective use of heat with vacuum centrifugal concentrators to enhance the drying process and, thereby, reduce processing time and provide a better specimen, is difficult to achieve. The transfer of heat from electrically heated hot plates or the like is extremely inefficient in a vacuum. Such heaters are therefore slow in this application and require considerable energy to operate.

One possibility is to use microwave energy to heat specimens in a vacuum centrifugal concentrator. Early attempts by the present inventor to use microwave energy showed that it was virtually impossible to attain meaningful heating rates at useful levels of vacuum due to the tendency for arcing under the electromagnetic field generated by the microwaves. Most of the energy is lost in arcing, thus preventing heating of the specimens, and also damaging the equipment.

OBJECTS AND SUMMARY OF THE INVENTION

Accordingly, it is an object of the invention to provide a vacuum concentrator which overcomes the drawbacks of the prior art.

It is a further object of the invention to provide a vacuum concentrator that heats a liquid substance to enhance the drying process.

It is a still further object of the present invention to heat the liquid substance by efficient application of microwave energy by suppressing its tendency to arc in a vacuum.

Briefly stated, the present invention provides a vacuum concentrator using microwave heating to enhance the rapid drying of a liquid specimen. Microwave heating without excessive arcing is made possible in a vacuum chamber by controlling the power of a microwave generator, by modifying antenna-like objects, by transmitting microwave energy from the microwave generator through a circular waveguide into the vacuum chamber, and by interposing air in a direct path between opposing edges of microwave injection slots, while maintaining the vacuum condition in the vacuum chamber. This can be accomplished using air filled plastic bosses passing through, and substantially filling the microwave injection slots. An alternate to the air filled bosses can be a non-metallic closure plate in the inside bottom of the vacuum chamber that seals the microwave injection slots from the vacuum chamber, while allowing energy to be injected freely into the chamber. The microwave energy not absorbed by the specimen is absorbed by a vacuum chamber cover and dissipated to the atmosphere as heat.

According to a feature of the invention, there is provided a vacuum centrifugal concentrator comprising: an enclosure, the enclosure having an open top, a lid means for closing the open top, a vacuum vessel having a rim in the enclosure, the lid forming an airtight seal with the rim, means for forming the airtight seal when contacted by the lid, the lid including a frame, legs of the frame being quarter wave microwave traps, the frame supporting a piece of boro-silicate glass, the glass being a microwave energy absorbing material, a metal screen covering at least one surface of the boro-silicate glass, at least one ferrite microwave absorber in the lid, a row of microwave fingers protruding downward from each the leg of the frame to seal the enclosure against microwave leakage, the vacuum vessel being a conductive metal, means in the vacuum vessel for supporting a centrifugal rotor, a well depending from the vacuum vessel, the means including a magnetic drive coupling suspended in the well, the well being vacuum sealed by a bottom wall, the bottom wall being made of non-ferromagnetic material for magnetic coupling of the magnetic drive coupling to a means, external to the well, for rotating the centrifugal rotor, a shaft, the magnetic drive coupling connected to a bottom end of the shaft, the shaft extending through and being rotatably supported by a metal bearing, an upper end of the shaft rotatably supporting a metallic hub of the centrifugal rotor, means for attaching the hub to the centrifugal rotor, a collar surrounding the shaft between the bearing and the hub to thicken and strengthen the shaft and inhibit microwave arcing to the shaft, a central support plate covering the well, the metal bearing supported axially by the central support plate, the support plate having an inner surface generally coplanar with an inner bottom surface of the vacuum vessel, the support plate being a conductive material to form a continuous conductive chamber in the vacuum vessel, the vacuum vessel including an annular series of slots along a bottom surface, radially between the depending well and an outer periphery of the vacuum vessel, means for injecting microwave energy into the vacuum in the vacuum vessel, the means for injecting microwave energy into the vacuum vessel including: a microwave generator, a waveguide for distributing microwave energy to the vacuum vessel, a beginning end of the waveguide coupled to the microwave generator, a terminal end of the waveguide for terminating the microwave energy, a top side of the waveguide for mounting the waveguide to a bottom of the vacuum vessel, the waveguide including a generally circular portion, the top side having a series of slots between the beginning end and the terminal end, the slots being effective for distributing the microwave energy to the vacuum vessel, the slots progressing slightly larger in size in a direction away from the microwave generator, an adjustment screw at each slot location for adjusting the waveguide for equal microwave power at each slot, slots in the bottom of the vacuum vessel generally aligned with corresponding slots in the waveguide, the slots in the bottom being substantially larger than the slots in the waveguide, a dielectric ring between the waveguide top the bottom of the vacuum vessel vacuum sealing the slots in the top side of the waveguide from the corresponding slots of the vacuum vessel, metallic gasketing between peripheries of the waveguide and the vacuum vessel, the waveguide being filled with air, and the dielectric ring including bosses fitting through, and substantially filling the slots in the vacuum vessel.

According to a further feature of the invention, there is provided a vacuum centrifugal concentrator comprising; an enclosure, the enclosure having an open top, a lid for closing the open top, a vacuum vessel having a rim in the enclosure, the lid forming an airtight seal with the rim, the lid including a frame, legs of the frame being quarter wave microwave traps, the frame supporting a piece of glass, the glass being a microwave energy absorbing material, a metal screen covering at least one surface of the boro-silicate glass, at least one ferrite microwave absorber in the lid, a row of microwave fingers or seal strips protruding downward from each leg of the frame, the microwave fingers to seal said enclosure against microwave leakage, the vacuum vessel being a conductive metal, means in the vacuum vessel for supporting a centrifugal rotor, a well depending from the vacuum vessel, the means including a magnetic drive coupling suspended in the well, the well being vacuum sealed by a bottom wall, the bottom wall being made of non-ferromagnetic material for magnetic coupling of the magnetic drive coupling to a means, external to the well, for rotating the centrifugal rotor, a shaft, the magnetic drive coupling connected to a bottom end of the shaft, the shaft extending through and being rotatably supported by a bearing, an upper end of the shaft rotatably supporting a metallic hub of the centrifugal rotor, means for attaching the metallic hub to the centrifugal rotor, a collar surrounding the shaft between the bearing and the metallic hub to thicken and strengthen the shaft and inhibit microwave arcing to the shaft, a central support plate covering the well, the bearing supported axially by the central support plate, the support plate having an inner surface generally coplanar with an inner bottom surface of the vacuum vessel, the support plate being a conductive material to form a continuous conductive chamber in the vacuum vessel, the vacuum vessel including an annular series of slots along a bottom surface, radially between the depending well and an outer periphery of the vacuum vessel, means for injecting microwave energy into a vacuum in the vacuum vessel, the means for injecting microwave energy into the vacuum vessel including; a microwave generator, a waveguide for distributing microwave energy to the vacuum vessel, a beginning end of the waveguide coupled to the microwave generator, a terminal end of the waveguide for terminating said microwave energy, a top side of the waveguide for mounting the waveguide to a bottom of the vacuum vessel, the waveguide including a generally circular portion, the top side having a series of slots between the beginning end and the terminal end, the slots being effective for distributing the microwave energy to the vacuum vessel, the slots progressing slightly larger in size in a direction away from the microwave generator, an adjustment screw at each slot location for adjusting the waveguide for equal microwave power at each slot, slots in the bottom of the vacuum vessel generally aligned with corresponding the slots in the waveguide, the slots in the bottom being substantially larger than the slots in the waveguide, a non-metallic closure plate an upper surface of the bottom of the vacuum vessel, vacuum sealing the slots in the bottom of the vacuum vessel the vacuum vessel, metallic gasketing between peripheries of the waveguide and the vacuum vessel, and the waveguide and the slots in the bottom of the vacuum vessel being filled with air.

According to a further feature of the invention, there is provided apparatus for injecting microwave energy into a metallic vessel comprising: a microwave generator, a waveguide receiving the microwave energy from the microwave generator, at least a first slot in the waveguide, at least a second slot in the metallic vessel, the first and second slots being generally aligned, a dielectric boss extending through, and substantially filling the second slot, a hollow in the dielectric boss, and the hollow extending into the vessel beyond an inner bottom thereof, whereby a direct path between opposing edges of the second slot must pass through the hollow.

According to a still further feature of the invention, there is provided a microwave heated vessel comprising: means for injecting microwave energy into the vessel, a lid for the vessel, the being a glass, and the glass being a microwave absorbent material.

According to a still further feature of the invention, there is provided a waveguide comprising: an energy-receiving end for receiving microwave energy, a terminating end, and a generally circular planform portion between the energy-receiving end and the terminating end.

According to a still further feature of the invention, there is provided apparatus for injecting microwave energy into a metallic vessel comprising: a microwave generator, a waveguide receiving said microwave energy from said microwave generator, at least a first slot in said waveguide, at least a second slot in said metallic vessel, said first and second slots being generally aligned, a dielectric closure plate in an inside bottom of said metallic vessel, said dielectric closure plate covering said second slot, means for sealing said closure plate to said metallic vessel to prevent air leakage between in interior of said metallic vessel and said first and second slots, an air groove in a surface of said dielectric closure plate aligned with said first and second slots, whereby air external to said metallic vessel is enabled to fill said groove, whereby a direct path between opposing edges of said second slot must pass through said air.

The above and other objects, features and advantages of the invention will become apparent from the following description of the preferred embodiment read in conjunction with the accompanying drawings, in which like reference numerals designate the same elements.

DETAILED DESCRIPTION OF THE PREFERRED EMBODIMENT

It is a basic problem to prevent arcing in an electromagnetic field at low atmospheric pressure. The dielectric strength of air at atmospheric pressure is substantially greater that at reduced pressure. Thus, as the pressure is reduced in a vacuum vessel, the tendency for arcing increases. Arcing is encouraged by pointed conducting objects, and by such objects having a substantial ratio of length to width. If the problem of arcing cannot be solved, microwave energy cannot be used in a vacuum concentrator.

Figure 1:
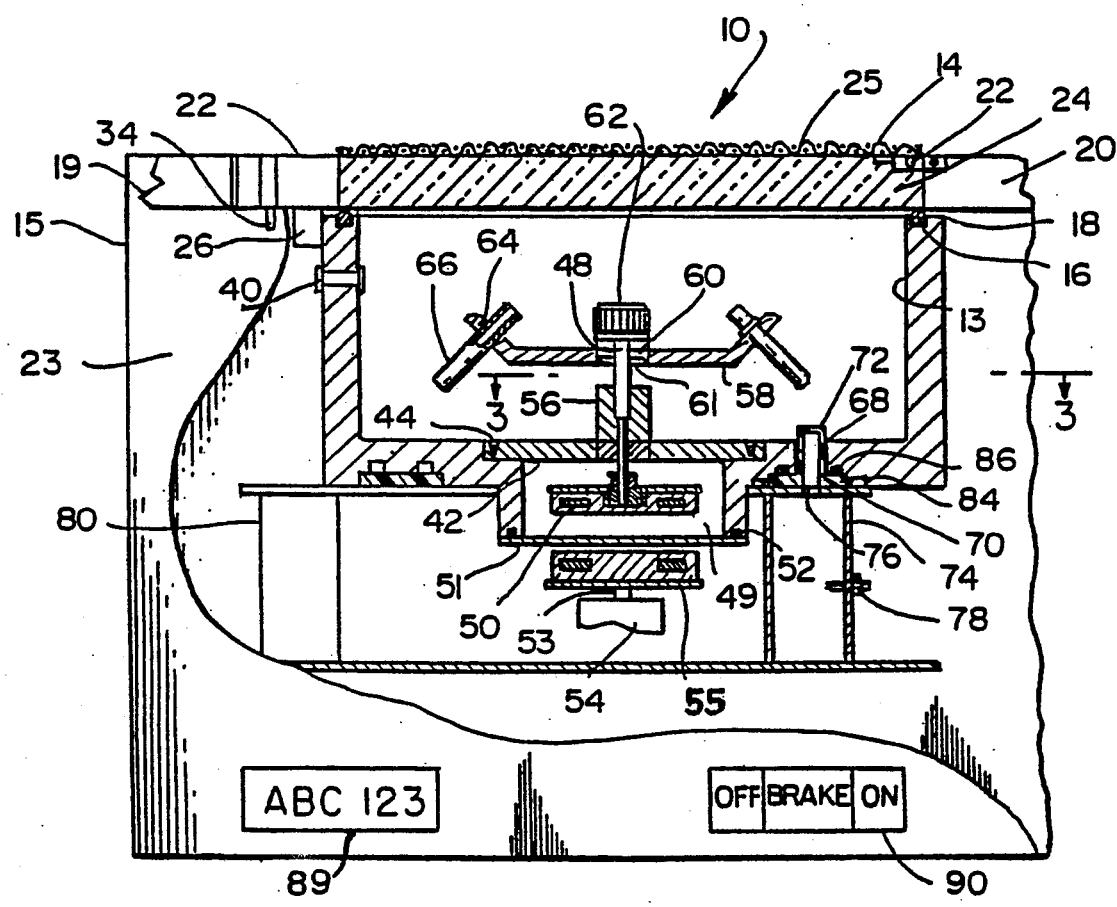
FIG. 1 is a cross section a preferred embodiment of the invention.

Referring to FIG. 1, a vacuum vessel 12 of a centrifugal concentrator 10, made of cast aluminum, or other electrically conductive material, is tightly closed by a lid 14 of an enclosure 15. An inner surface 13 of vacuum vessel 12 is coated with soil-releasing material such as, for example a fluorocarbon coating. An elastomeric ring 16, projecting upwardly from and disposed around a rim 18 of vacuum vessel 12, creates a vacuum seal with lid 14.

Figure 2:
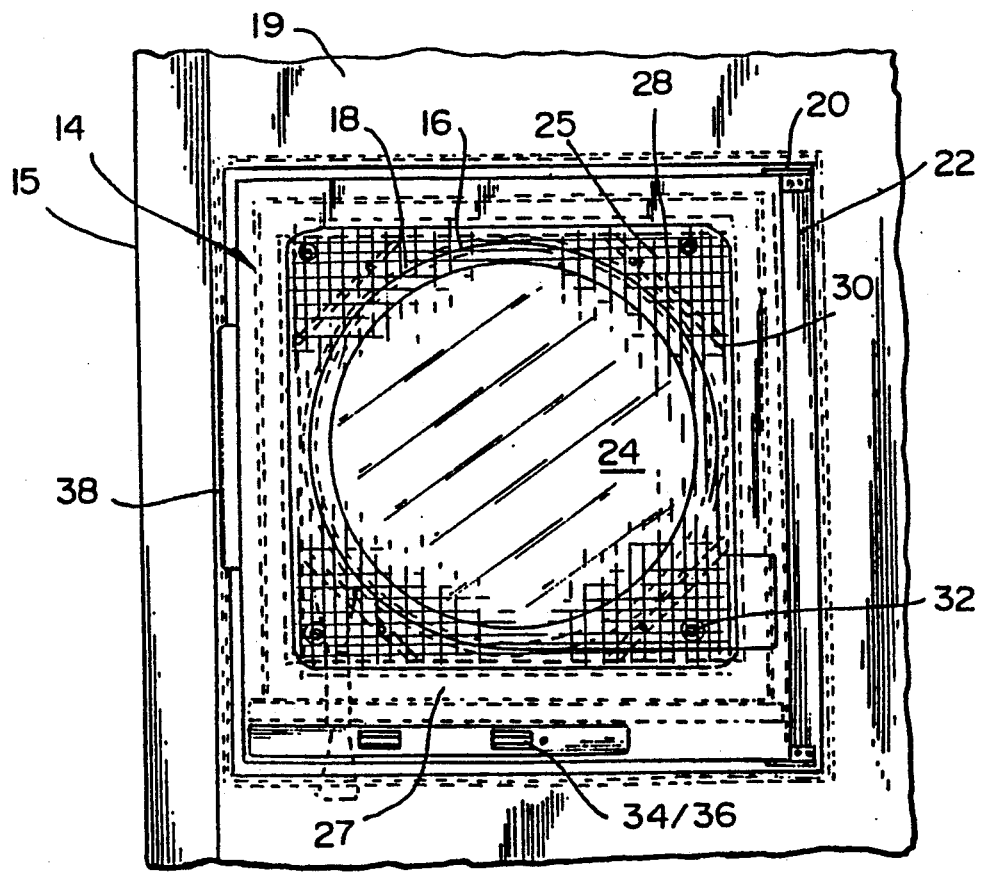
FIG. 2 is a plan view of the lid of the invention of FIG. 1.

Referring to FIG. 2, enclosure 15 comprises an outer frame assembly 19 that liftably supports a lid frame 22 of lid 14 by means of hinges 20. Lid frame 22 surrounds and supports a boro-silicate glass cover 24. A fine metal screen 25, preferably of stainless steel, is disposed above glass cover 24. Metal screen 25 acts as a microwave shield for vessel 12. The boro-silicate glass of glass cover 24 is itself a microwave absorber. The combination of shielding by metal screen 25 and radar absorption by glass cover 24 prevents leakage of any substantial microwave radiation therethrough.

Around the periphery of lid frame 22, a plurality of microwave fingers or seal strips 26 form a microwave seal with enclosure 15 preventing microwave leakage when lid 14 is in its closed position during operation. Quarter wave traps 27 form the four sides of lid frame 22. As is well known, a quarter wave trap is seen as a short circuit by a source of microwave energy within vacuum vessel 12. Such a short circuit prevents leakage of microwave energy past the perimeter of lid frame 22.

As an additional measure to prevent leakage of microwave energy, a ferrite microwave absorber 28 is disposed at each corner of lid frame 22, supported by a retainer plate 30 and a screw 32. Interlock latches 34, that prevent lifting of lid 14 during operation, are located on the side of lid frame 22 to engage receptacles 36 in lid frame 22.

A handle 38 is attached on the forward edge of lid frame 22 to permit raising and lowering of lid 14.

Referring again to FIG. 1, a vacuum fitting 40 passes through the wall of vacuum vessel 12 for the attachment of a vacuum pump (not shown) to vacuum vessel 12.

A central well 49 depends from the bottom of vacuum vessel. A metallic support plate 42, preferably of aluminum, covers central well 49. Support plate 42 may be coated on its upper surface with a soil-release material such as, for example, a fluorocarbon coating. A plurality of screws 44 secure support plate 42 to vacuum chamber 12. Screws 44 are countersunk and flat-headed so that they do not form projections into the body of vacuum chamber 12 where they might act as antennas and thereby encourage arcing of microwave energy to the body of vacuum chamber 12. In a standard vacuum concentrator, such as disclosed in the referenced patent, the element corresponding to support plate 42 is made of plastic. A plastic support plate would permit arcing of microwave energy from the perimeter of central well 49. The use of metal for support plate 42, and countersunk flat-headed screws 44 presents a substantially unbroken, flat bottom of vacuum chamber 12, thereby substantially reducing the tendency for arcing in this vicinity.

A bearing assembly 46 is mounted centrally to the bottom of support plate 42 and rotatably supports a shaft 48, which extends therethrough and is journalled within the axis of bearing assembly 46.

A magnetic-drive shaft coupler 50 is axially attached to a bottom end of shaft 48, thereby placing shaft coupler 50 near the bottom of central well 49. The bottom of central well 49 is closed by a bottom wall 51. A vacuum-tight seal between bottom wall 51 and central well 49 is assured by an elastomeric O-ring 52.

Beneath bottom wall 51 a drive shaft 53 of a motor 54 drivably supports a magnetic motor coupler 55 that is in axial alignment with shaft coupler 50. When motor coupler 55 is rotated by motor 54, shaft coupler 50 rotates with it as a result of magnetic coupling.

A bearing housing 56, into which bearings 46 are pressed, together with a metal central hub 60 of plastic rotor 58, increases the effective diameter of shaft 48. This increase in effective diameter produces a much smaller length-to-diameter ratio, thus reducing the tendency for it to act as a microwave antenna that would encourage arcing. This helps reduce the likelihood of arcing.

Plastic rotor 58 with central hub 60 is affixed to an upper end of shaft 48 by a plastic retainer knob 62. A key 61 passing through shaft 48 engages central hub 60 so that central hub 60 and rotor 58 rotate with shaft 48. Plastic is used for retainer knob 62 to further avoid the possibility of there being an effective antenna within vacuum vessel 12 that might divert microwave energy away from the substance being concentrated.

Rotor 58 is provided with one or more annular rows of tube holders 64 each one of which is sized to hold a test tube 66 of substance to be concentrated.

Figure 3:
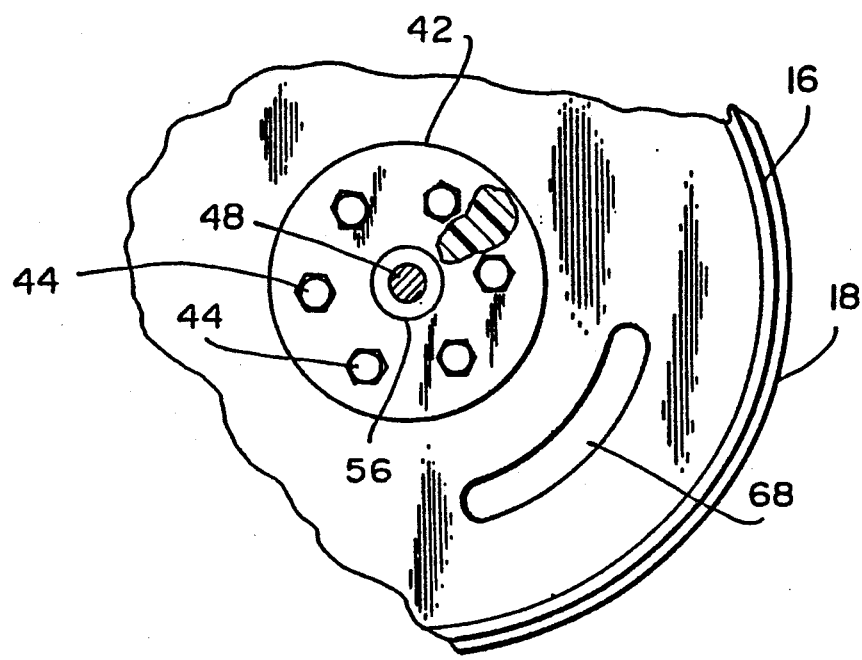
FIG. 3 is a fragment of a cross section of the invention, taken along line III—III of FIG. 1.

Referring to FIG. 3, a plurality of microwave slots 68 are disposed around the bottom of vacuum vessel 12 to provide windows for coupling of microwave energy from a waveguide 74.

Figure 4:
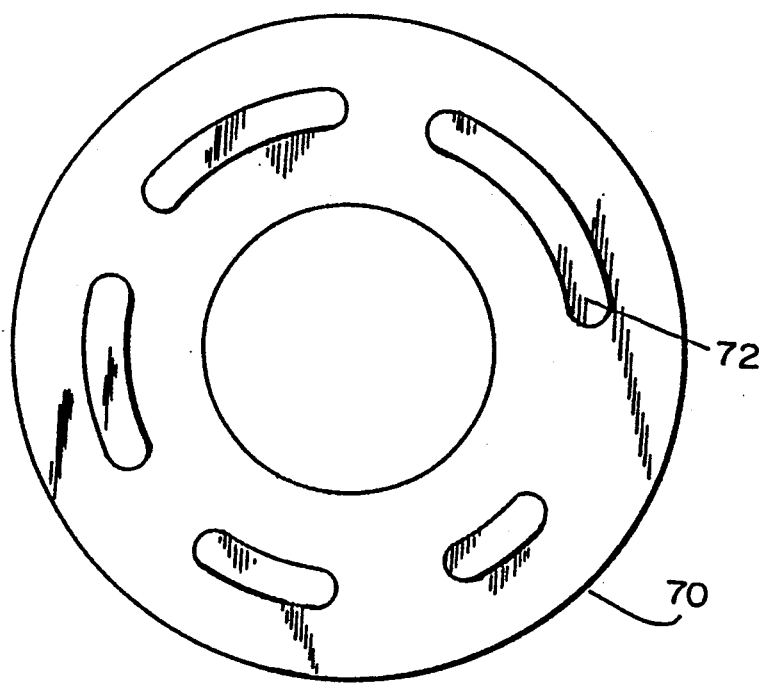
FIG. 4 is a top view of the vacuum ring.

Referring now to FIG. 4, a vacuum ring 70, preferably of a high-dielectric plastic resin such as, for example, TEFLON, is disposed below the bottom of vacuum vessel 12. Vacuum ring 70 seals microwave slots 68 in the bottom of vacuum vessel 12 to prevent vacuum leakage. In addition, vacuum ring 70 includes a plurality of hollow bosses 72 which project upward through microwave slots 68.

Figure 6:
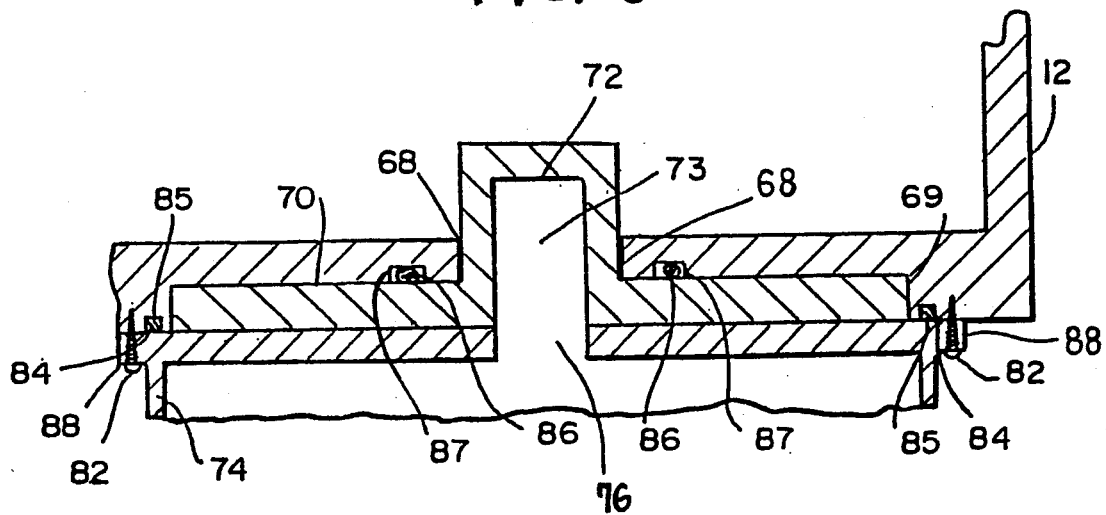
FIG. 6 is an enlarged cross section showing the interface between the slotted waveguide and the vacuum vessel of the vacuum centrifugal concentrator of FIG. 1.

Referring momentarily to FIG. 6, each boss 72 includes a hollow opening 73 which extends above the level the bottom of vacuum vessel 12. During use, vacuum vessel 12 above bosses 72 is exposed to a vacuum. However, the region below bosses 72 is at normal atmospheric pressure. Thus, a direct path between opposing edges of a microwave slot 68 must cross the high dielectric of TEFLON plastic and the relatively high dielectric of atmospheric-pressure air. As a consequence of the high-dielectric materials in the direct path between opposing edges of each microwave slot 68, arcing on these paths is inhibited.

Figure 5:
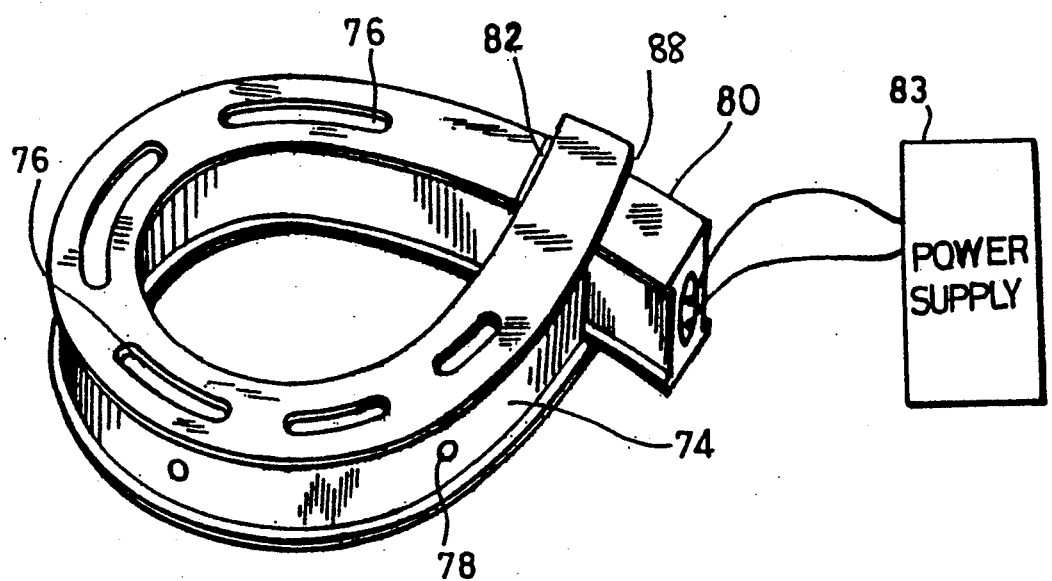
FIG. 5 is a perspective view of the magnetron microwave generator and the slotted waveguide of the invention of FIG. 1.

As shown in FIG. 5, a circular waveguide 74 is coupled to a conventional magnetron microwave oscillator 80. A series of five arcuate waveguide slots 76 are arranged annularly in the upper surface of circular waveguide 74. Waveguide slots 76 vary in size with the smallest slot being closest to magnetron microwave oscillator 80 and the largest slot closest to a terminal end 82 so that the power passing through all waveguide slots is substantially equal. An adjustment screw 78, disposed downstream of each waveguide slot 76, further adjusts microwave distribution to further assure that the power at each waveguide slot 76 is equal, and that there is uniform distribution of microwave energy in vacuum vessel 12.

In the preferred embodiment, it was found that low power microwave avoided the arcing that tends to occur in a small vacuum vessel and that a 500 watt output of a conventional microwave oscillator 80 caused arcing that could not be suppressed easily. In order to attain a level of power which could be more easily handled, the power output of a power supply 83 for magnetron microwave oscillator 80 was reduced to a value providing about 150 watts of microwave energy. However, for a larger vacuum vessel, more power may be used.

Returning now to FIG. 6, an annular groove 69 in the bottom of vacuum vessel 12 receives vacuum ring 70, with bosses 72 passing upward through their respective microwave slots 68. A pair of O-rings 86 in parallel O-ring grooves 87 are disposed around the bottom of vacuum vessel 12 on opposite sides of the series of microwave slots 68 to form a vacuum seal between vacuum ring 70 and the surface of annular groove 69. A pair of microwave gaskets 84 are fitted into respective gasket grooves 85 in the bottom of vacuum vessel 12 on opposite sides outboard of annular groove 69. Circular waveguide 74 includes inner and outer flanges 88 extending beyond gasket grooves 85. A plurality of screws 82 are affixed through flanges 88 and into the bottom of vacuum vessel 12 to hold circular waveguide firmly in place against the bottom of vacuum vessel 12. Tightening of screws 82 compresses O-rings 86 to create a vacuum seal, and also compresses microwave gaskets 84 to create an RF seal.

Note that each microwave slot 68 of vacuum vessel 12 is slightly larger than its corresponding waveguide slot 76 of circular waveguide 74 to assure efficient coupling of microwave energy from circular waveguide 74 to vacuum vessel 12.

The embodiment of the invention described above has been found to be very effective for injecting microwave energy into vacuum vessel 12. During use, however, it was discovered that residual arcing occasionally perforated one of bosses 72, thus losing the necessary vacuum seal. Replacement of vacuum ring 70 required substantial disassembly of the entire centrifugal concentrator 10. This resulted in substantial downtime.

Figure 7:
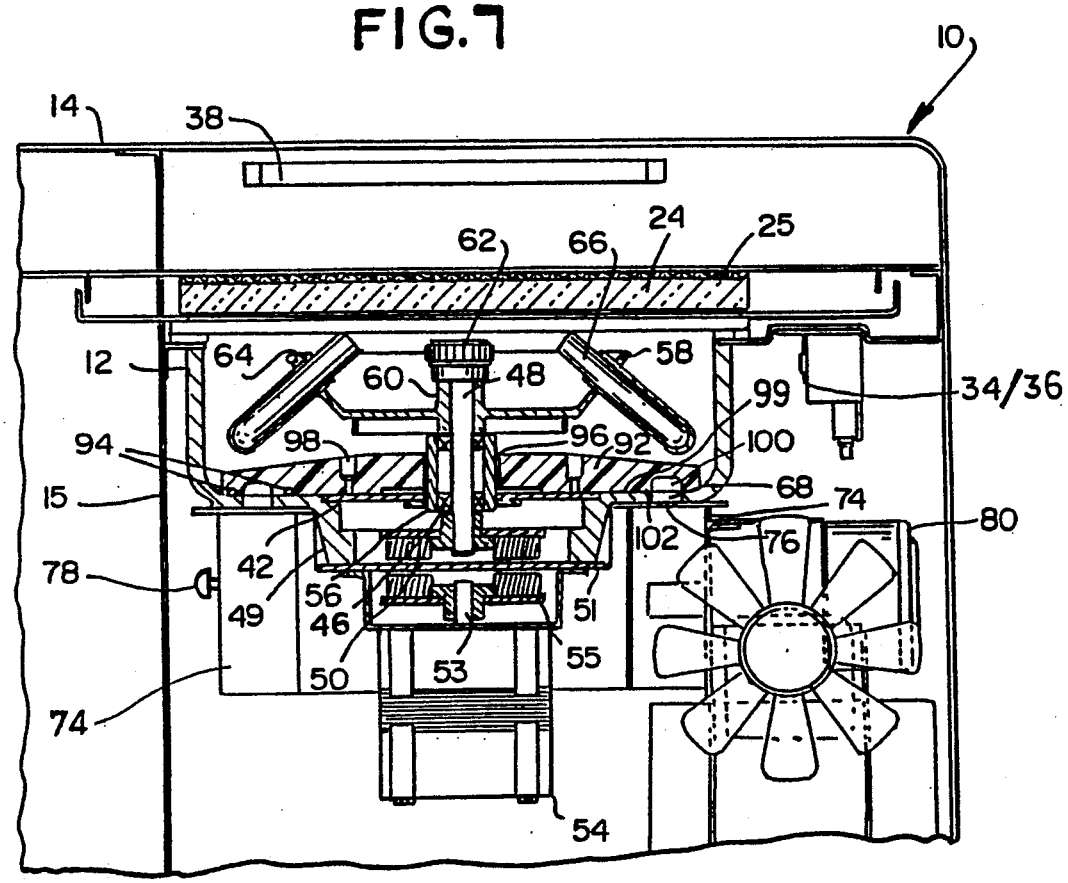
FIG. 7 is a cross section of a second preferred embodiment of the invention.

Referring to FIG. 7, there is shown a second preferred embodiment of the invention which reduces the downtime in the event of perforation. In this embodiment, vacuum ring 70 and bosses 72 together with vacuum sealing rings 86 (shown in FIGS. 1 and 6) are replaced by a non-metallic disk shaped closure plate 92 located inside the bottom of vacuum vessel 12. An axial hole 96 of closure plate 92 surrounds bearing housing 56 inside vacuum vessel 12. A plurality of recessed screws 98 secure closure plate 92 to an upper surface 99 of the bottom of vacuum vessel 12. Vacuum sealing rings 94, disposed across an annular air groove 100 on under surface 102 of closure plate 92, form an airtight seal between closure plate 92 and vacuum vessel 12 to maintain a vacuum in vacuum vessel 12 during operation.

Annular air groove 100 is coincident with the series of microwave slots 68 that are disposed around the bottom of vacuum vessel 12 in order to allow air to fill microwave slots 68 and air groove 100 above them. The air that fills microwave slots 68 and air groove 100 discourages microwave energy from arcing across microwave slots 68 in the same manner as do bosses 72 (shown in FIG. 6) described earlier.

Instead of a single annular groove 100, the same function may be performed by a sequence of arcuate grooves, arranged annularly, and aligned with corresponding slots in the bottom of vacuum vessel 12. This arrangement is presently considered to be the preferred embodiment.

A major advantage of this embodiment over the first described embodiment is that should the vacuum seal between closure plate 92 and the bottom of pressure vessel 12 fail, replacement can be made from the top of vacuum vessel 12 without requiring disassembly of the entire centrifugal concentrator 10 or affecting the integrity of the microwave seal.

Referring again to FIG. 1, an indicator 88 displays the status of the operation of centrifugal concentrator 10. A control panel 90 controls the operation of the device.

Because the operation of a vacuum centrifugal concentrator is fully disclosed in U.S. Pat. No. 4,226,669, only the operation of the microwave heating portion of the present invention is described below.

Referring to FIG. 1, when lid 14 is closed, centrifugal concentrator 10 is effectively sealed against microwave leaks by the action of microwave fingers or seal strips 26 that microwave seal lid 14 to enclosure 15. Lid 14 is made microwave proof by metal screen 25 above glass cover 24, quarter wave microwave traps 27 and ferrite microwave absorbers 28. Glass 24, being fabricated of boro-silicate glass also serves as an RF load, dissipating any remaining microwave energy. In addition, microwave gasket 84 prevents microwave leakage past the interface between vacuum vessel 12 and circular waveguide 74.

Microwave leakage from the floor of vacuum vessel 12 is sealed by metal support plate 42 and metal shaft 48. The result is a continuous metallic conductive chamber that eliminates all microwave leakage.

The microwave security of centrifugal concentrator 10 is further assured by interlock latches 34, which prevent the operation of the microwave heating when lid 14 is open and which prevent lid 14 from being opened during operation.

Because TEFLON is an insulator having a relatively high dielectric constant, the presence of this plastic resin between opposed edges of microwave slots 68 tends to reduce the likelihood of arcing. In addition, since the centers of bosses 72 are hollowed to produce hollow openings that extend above the bottom of vacuum vessel 12, the atmospheric-pressure air thus placed in the path between opposed edges of microwave slots 68 futher reduces the likelihood of arcing.

Tests were performed using a flat ring, without bosses 72, in place of vacuum ring 70. Arcing between the opposed edges of microwave slots 68 took place at levels of vacuum that were insufficient to accelerate driving of specimens. The arcing was destructive of vacuum vessel 12. In addition, the arcing tended to melt the flat ring, whereby the vacuum seal was broken after a relatively short operating life. With bosses 72 providing atmospheric-pressure air within microwave slots 68, and the height microwave absorbing capability of lid 14, microwave heating, without substantial arcing is possible down to a vacuum below 1 torr.

In the second preferred embodiment, discussed with reference to FIG. 7, air is allowed to fill microwave slots 68 with the vacuum seal provided by closure plate 92 above microwave slots 68. This eliminates the need for the bosses 72 used in the embodiment of FIG. 1 with the same reduction in arcing. As with the embodiment of FIG. 1, the high microwave energy absorbing ability of lid 14 enables operation without substantial arcing in vacuums of below 1 torr.

When power is applied to power supply 83 (shown in FIG. 5) by the operation of switch, power supply 83 energizes magnetron microwave oscillator 80. The microwave output of magnetron microwave oscillator 80 is distributed evenly, through waveguide slots 76 and microwave slots 63 around the bottom of vacuum vessel 12, with about 30 watts to each slot for a 150 watt magnetron microwave oscillator 80, to propagate evenly throughout vacuum vessel 12. Tuning screws 78 are adjusted during factory calibration to assure the even distribution of the microwave energy. In other embodiments of the invention, tuning screws 78 may be omitted or be replaced with other tuning devices.

The microwave energy travels to and heats the specimen in test tube 66, while excess energy that is not absorbed by the specimen is absorbed by the lid 14 and dissipated as heat.

Having described the preferred embodiments of the invention with reference to the accompanying drawings, it is to be understood that the invention is not limited to those precise embodiments, and that various changes and modifications may be affected therein by one skilled in the art without departing from the scope or spirit of the invention as defined in the appended claims.

What is claimed is:

1. A vacuum centrifugal concentrator comprising
a vacuum vessel having a centrifugal rotor rotatably mounted within an interior thereof,
means for injecting microwave energy into said vacuum vessel interior,
means for preventing electrical arcing in said interior when a vacuum condition is imposed therein, the microwave energy injection means including
a microwave generator and a waveguide, said waveguide having a first end coupled to said microwave generator and a second end embodying microwave energy terminating means, at least a portion of said waveguide between its first and second ends describing a portion of a circle,
an upper part of said waveguide being mounted to a bottom of said vacuum vessel, said waveguide upper part having a series of waveguide slots located therein in the circle describing portion thereof, successive ones of said slots being progressively larger size in a direction away from said microwave generator, there being a plurality of slots in the bottom of said vacuum vessel, and
said vessel bottom slots having a substantially one-to-one alignment with said waveguide slots, whereby microwave energy can be propagated from said waveguide into said vacuum vessel interior.

2. The vacuum centrifugal concentrator according to claim 1 further comprising at least one means for adjusting the amount of microwave energy that can pass through one bottom slot and a waveguide slot aligned therewith.

3. The vacuum centrifugal concentrator according to claim 2, wherein said at least one means for adjusting includes a screw protruding into said waveguide.

4. The vacuum centrifugal concentrator according to claim 2, wherein said at least one means for adjusting adjusts microwave distribution at each waveguide slot to be equal.

5. The vacuum centrifugal concentrator of claim 1 in which said vacuum vessel is of conductive metal, and a well is centrally located in the bottom thereof, and
a metal support plate covering the well and disposed flush with said vacuum vessel bottom.

6. The vacuum centrifugal concentrator of claim 1 in which the centrifugal rotor includes a shaft, and the electrical arcing prevention means includes a collar encircling the shaft to increase shaft effective diameter thereby reducing shaft length/diameter ratio and correspondingly reducing shaft tendency to act as a microwave antenna.

7. The vacuum centrifugal concentrator of claim 1 further comprising
a dielectric vacuum ring intervening the mounting of the waveguide upper part to the vacuum vessel bottom,
means for vacuum sealing said dielectric ring to said vessel bottom thereby to prevent vacuum leakage through the vessel slots,
a plurality of bosses in said dielectric ring, each boss passing through and substantially filling one of the vessel slots, and
means defining a hollow in a lower part of each boss, the hollow extending upward above an inner surface of said vessel bottom whereby a direct path between opposed edges of each vessel slot must pass through a hollow.

8. The vacuum centrifugal concentrator of claim 7 in which the hollows are in communication with atmospheric air.

9. The vacuum centrifugal concentrator of claim 1 further comprising
a non-metallic vacuum closure plate disposed on an upper surface of said vacuum vessel bottom,
means for vacuum sealing the closure plate to said upper surface thereby to prevent vacuum leakage through the slots in the vessel bottom, the closure plate having recessed blind arcuate grooves coincident with the vessel bottom slots, said arcuate grooves being in communication with atmospheric air whereby a direct path between opposed edges of each vessel bottom slot must pass through said air.

10. The vacuum centrifugal concentrator of claim 1 in which the microwave energy injection means includes a waveguide fixed to the vacuum vessel, and
gasket means effective to prevent microwave energy leakage intervening the waveguide and the vacuum vessel.

11. The vacuum centrifugal concentrator of claim 1 further comprising a cover for the vacuum vessel, said cover being a microwave-absorbing material.

12. The vacuum centrifugal concentrator of claim 11 in which said microwave-absorbing material is boro-silicate glass which is microwave energy absorptive.

13. The vacuum centrifugal concentrator of claim 1, further comprising:

a cover for said vacuum vessel; and said cover includes a metallic microwave screen.

14. The vacuum centrifugal concentrator of claim 13 further comprising at least one ferritemicrowave absorber adjacent the cover, the absorber being effective to absorb microwave energy.

15. The vacuum centrifugal concentrator of claim 1, further comprising:
a lid on said vacuum vessel: and at least one interlock latch to control opening of said lid.

16. A vacuum centrifugal concentrator comprising
an enclosure having an open top and a lid for closing said top, a vacuum vessel of a conductive metal, the vessel having a rim disposed in said enclosure with the lid forming an airtight seal with the rim, the lid including a frame comprised of frame parts defining quarter wave microwave traps,
a microwave energy absorbing glass piece supported by the frame with a metal screen covering at least one surface of the glass piece, the lid frame embodying ferrite microwave absorber means thereon,
a row of microwave seal strips carried on the frame parts for sealing said enclosure against microwave leakage,
a centrifugal rotor rotatably supported within an interior of said vacuum vessel, there being a well depending from a bottom of said vacuum vessel, the rotor including a shaft extending from the rotor into said well,
a magnetic drive coupling element carried in said well and connected to a lower end of said shaft, an upper end of the shaft being received in a metallic rotor hub, there being a shaft support bearing and housing therefor encircling the shaft intermediate the shaft upper and lower ends, the rotor hub and bearing housing increasing shaft effective diameter to decrease shaft length/diameter ratio and correspondingly the tendency of the shaft to act as a microwave antenna,
another power-driven magnetic coupling element disposed externally of said well and cooperating with the first-mentioned magnetic coupling element for rotating said rotor,
the bottom of the vacuum vessel including a series of slots disposed therein in an annular course located radially exterior of the well,
a microwave generator for injecting microwave energy into the vacuum vessel,
an air-filled waveguide disposed at a lower surface of the vessel bottom for distributing the microwave energy within said vacuum vessel, the waveguide having a beginning end coupled to the microwave generator and a terminal opposite end for terminating microwave energy flow, the waveguide intermediate said beginning and terminal ends thereof having a circular plan portion, the waveguide being mounted to the bottom of the vacuum vessel and having a series of slots therein in correspondence to and aligned with the slots in the vessel bottom, said slots being progressively larger in size in a direction away from the waveguide beginning end, with the slots in the vessel bottom being substantially larger in size than those in the waveguide, and
a dielectric ring intervening the waveguide and the vacuum vessel bottom lower surface for sealing the slots in the waveguide from the corresponding slots in the vessel bottom,
said dielectric ring including bosses extending through the vacuum vessel slots and upwardly a distance from the vessel bottom, the bosses including means defining hollows therein, the hollows being open to the air in the waveguide.

17. The vacuum centrifugal concentrator according to claim 16, wherein said microwave generator produces from about 10 to about 580 watts of microwave energy.

* * * * *